(12) United States Patent
Ishikita (10) Patent No.: US 11,224,716 B2
(45) Date of Patent: Jan. 18, 2022

(54) RELIEF VALVE

(71) Applicant: Naoyuki Ishikita, Gunma (JP)

(72) Inventor: Naoyuki Ishikita, Gunma (JP)

( * ) Notice: Subject to any disclaimer, the term of this patent is extended or adjusted under 35 U.S.C. 154(b) by 693 days.

(21) Appl. No.: 16/067,192

(22) PCT Filed: Dec. 28, 2016

(86) PCT No.: PCT/JP2016/089187
§ 371 (c)(1),
(2) Date: Jun. 29, 2018

(87) PCT Pub. No.: WO2017/115866
PCT Pub. Date: Jul. 6, 2017

(65) Prior Publication Data
US 2019/0022346 A1    Jan. 24, 2019

(30) Foreign Application Priority Data

Dec. 31, 2015   (JP) ............................. JP2015-257752

(51) Int. Cl.
*A61M 16/20* (2006.01)
*A61M 16/01* (2006.01)
(Continued)

(52) U.S. Cl.
CPC ............ *A61M 16/209* (2014.02); *A61H 1/00* (2013.01); *A61H 9/005* (2013.01); *A61H 9/0078* (2013.01);
(Continued)

(58) Field of Classification Search
CPC .. A61M 16/00; A61M 16/0003; A61M 16/20; A61M 16/201; A61M 16/206;
(Continued)

(56) References Cited

U.S. PATENT DOCUMENTS 2,588,157 A    3/1952   Olson
4,932,434 A *  6/1990   Taylor ................... F16K 17/06
                                                       137/469

(Continued)

FOREIGN PATENT DOCUMENTS

CN       105102869 A    11/2015
GB       949221         2/1964
(Continued)

OTHER PUBLICATIONS

Office Action (Notification of the Second Office Action) dated Feb. 3, 2020, by the State Intellectual Property Office of the People's Republic of China in corresponding Chinese Patent Application No. 201680068564.6, and an English Translation of the Office Action. (12 pages).

(Continued)

*Primary Examiner* — Colin W Stuart
(74) *Attorney, Agent, or Firm* — Cermak Nakajima & McGowan LLP; Tomoko Nakajima (57) ABSTRACT

A relief valve in which a valve body is automatically properly opened/closed by pressure of gas while having a simple device structure, and a device including the relief valve. In a valve-closed state, a first pressure receiving surface portion receives pressure of gas from a valve hole to smoothly open a valve body, and in an open position after the valve is opened, a pressure receiving area is enlarged to a second pressure receiving surface portion, and the first pressure receiving surface portion and the second pressure receiving surface portion are surrounded by a peripheral wall portion formed on a back surface of the valve body. Thus, the valve body continuously receives the pressure with the pressure of the gas being reduced, thereby allowing the valve-opened state of the valve body to be stably maintained to set pressure.

13 Claims, 6 Drawing Sheets

(51) Int. Cl.
*F16K 17/06* (2006.01)
*F16K 17/04* (2006.01)
*A61H 1/00* (2006.01)
*A61H 9/00* (2006.01)
*A61H 31/02* (2006.01)

(52) U.S. Cl.
CPC .............. *A61H 31/02* (2013.01); *A61M 16/01* (2013.01); *F16K 17/04* (2013.01); *F16K 17/0413* (2013.01); *F16K 17/06* (2013.01); *A61H 2031/025* (2013.01)

(58) Field of Classification Search
CPC .............. A61M 16/207; A61M 16/208; A61M 16/209; A61M 16/01; A61M 39/22; A61M 39/24; A61M 39/26; A61M 2039/2433; A61M 2039/2473; A61M 2039/2486; A61M 2039/2493; A61M 2039/266; A61M 2039/267; A61M 2039/268; A61H 7/0078; F16K 17/04; F16K 17/0413; F16K 17/06
See application file for complete search history.

(56) References Cited

U.S. PATENT DOCUMENTS

| | | | |
|---|---|---|---|
| 5,094,266 A | 3/1992 | Ledbetter | |
| 9,482,354 B2* | 11/2016 | Girard | F16K 17/044 |
| 9,964,217 B2* | 5/2018 | Siebert | F16K 1/54 |
| 2005/0187500 A1* | 8/2005 | Perry | A61H 9/0078 601/152 |
| 2006/0021661 A1* | 2/2006 | Koch | F16K 15/028 137/543.19 |
| 2006/0157116 A1 | 7/2006 | Martin et al. | |
| 2012/0012111 A1* | 1/2012 | Howe, Jr. | A61M 16/208 128/205.12 |
| 2013/0118484 A1 | 5/2013 | Ishikita | |
| 2016/0010753 A1 | 1/2016 | Siebert | |

FOREIGN PATENT DOCUMENTS

| | | |
|---|---|---|
| JP | 47-10873 Y1 | 4/1972 |
| JP | 2005-288045 A | 10/2005 |
| JP | 2011-182949 A | 9/2011 |

OTHER PUBLICATIONS

Extended European Search Report dated Jun. 25, 2019 in corresponding European Patent Application No. 1688184 0.9.
International Search Report (PCT/ISA/210) dated Mar. 14, 2017, by the Japanese Patent Office as the International Searching Authority for International Application No. PCT/JP2016/089187.
Written Opinion (PCT/ISA/237) dated Mar. 14, 2017, by the Japanese Patent Office as the International Searching Authority for International Application No. PCT/JP2016/089187.

* cited by examiner

RELIEF VALVE

TECHNICAL FIELD

The present invention relates to a relief valve, and more particularly to a relief valve in which a valve body is automatically opened/closed by pressure of gas without using an electric drive source for an opening/closing operation of the valve body. The present invention also relates to various devices using the relief valve.

BACKGROUND ART

The present applicant has proposed an anesthetic inhalation aid device that can be easily handled and enables prompt inhalation administration of an anesthetic to a patient, as a device that terminates convulsions as soon as possible after the start of a convulsive seizure induced by recurrent excessive firing of brain neurons (Patent Literature 1). The anesthetic inhalation aid device atomizes the anesthetic to be mixed with air or oxygen gas to generate mixed gas, and the mixed gas is supplied to the patient through a mixed gas introduction passage including an inhalation mask, an artificial nose unit, a tube, or the like by manually compressing an elastic bag. When pressure of the gas in the mixed gas introduction passage reaches predetermined pressure, a valve body of a relief valve is separated from a valve seat, and a part of the mixed gas is discharged through an exhaust port to the outside. Thus, the anesthetic inhalation aid device can be safely used without excessive strain on respiratory organs of the patent.

CITATION LIST

Patent Literature

Patent Literature 1: WO2012/165541

SUMMARY OF INVENTION

Technical Problem

The present applicant has made continual trial manufactures and improvements to put the anesthetic inhalation aid device described above into practical use, and found that stably maintaining a valve-opened state of a relief valve would be one important key factor for success in practical use. Specifically, the conventional relief valve has a valve seat of a hemispherical shape in a valve casing, and the valve body is formed as a hemispherical protrusion without a substantial gap between the valve body and the valve seat to prevent mixed gas from flowing out in a valve-closed state in which the valve body is seated on the valve seat. However, for the conventional relief valve having the hemispherical valve seat and valve body, although the valve-opened state is obtained at predetermined set pressure, the mixed gas smoothly flows between the valve seat and the valve body after the valve is opened, and it is difficult to use the hemispherical protrusion of the valve body as a pressure receiving surface to receive pressure of the mixed gas and maintain the valve-opened state.

Also, the present applicant has found that the relief valve can be applied as a pressure regulating valve in various devices that use gas as an actuating mechanism in the process of continual improvements of the conventional relief valve as a key device for the anesthetic inhalation aid device, and diligently studied the applications.

The present invention has been made in the process of improvements of the conventional relief valve as described above. The present invention has an object to provide a relief valve in which a valve body is automatically properly opened/closed by pressure of gas while having a simple device structure.

The present invention also has an object to provide various devices using this relief valve.

Solution to Problem

To achieve the objects, the present invention is configured as described below.

Specifically, the present invention provides a relief valve including: a suction port formed into a cylindrical shape and opening on one end side in a cylinder axial direction; a valve hole communicating with the suction port; a valve casing having a valve chamber communicating with the valve hole; a valve body that closes the valve hole in a valve-closed state, and is raised in the cylinder axial direction by pressure of gas flowing from the suction port to open the valve hole; and a biasing member that biases the valve body toward the valve hole, wherein the valve body includes a first pressure receiving surface portion that closes the valve hole in the valve-closed state and receives the pressure of the gas flowing from the valve hole, a second pressure receiving surface portion that receives the pressure of the gas flowing from the valve hole into the valve chamber in a valve-opened state in which the valve body opens the valve hole, and a peripheral wall portion that cylindrically extends from the second pressure receiving surface portion along an inner peripheral surface of the valve casing.

According to the present invention, the relief valve can be achieved in which the valve body is automatically opened/closed by pressure of gas higher than set pressure at which the biasing member causes the valve body to close the valve hole, while having a simple device structure including the cylindrical valve casing, the valve body, and the biasing member without requiring an electric drive source for an opening/closing operation of the valve body.

Specifically, the valve body in the present invention includes the first pressure receiving surface portion that closes the valve hole in the valve-closed state and receives the pressure of the gas flowing from the valve hole. Thus, the first pressure receiving surface portion having a small pressure receiving area that closes the valve hole in the valve-closed state receives the pressure higher than the set pressure, thereby allowing smooth opening of the valve.

The valve body in the present invention includes the second pressure receiving surface portion that receives the pressure of the gas flowing from the valve hole into the valve chamber in the valve-opened state in which the valve body opens the valve hole, and the peripheral wall portion that surrounds the second pressure receiving surface portion and cylindrically extends along the inner peripheral surface of the valve casing. Thus, after the valve is opened, the pressure receiving area increases to the second pressure receiving surface portion, and the cylindrical peripheral wall portion surrounds the second pressure receiving surface portion. Thus, the first pressure receiving surface portion, the second pressure receiving surface portion, and the peripheral wall portion continuously receive the pressure with the pressure of the gas being reduced, thereby allowing the valve-opened state to be stably maintained to the set pressure. As such, the present invention can achieve the relief valve in which the valve body is automatically opened/closed by pressure of gas, while having a simple device structure without requiring an electric drive source for an opening/closing operation of the valve body.

The present invention may further include a pressure regulating member that presses the biasing member that biases the valve body to provide variable actuating pressure for the valve body to open the valve hole, on the other end side of the valve casing in the cylinder axial direction. The pressure regulating member may be configured to have an operating surface in which an exhaust port communicating with the valve chamber opens.

Accordingly, varying a pressing level of the pressure regulating member on the biasing member can easily vary the actuating pressure of the valve body. For example, in the case where the relief valve of the present invention is used in an artificial respirator, continuous artificial respiration with high pressure is required when a patient has airway narrowing due to swelling caused by bronchitis or tumor and laterality in lung expansion. Operating the pressure regulating member allows the actuating pressure of the valve body to the extent that both lungs properly work.

The pressure regulating member has the operating surface in which the exhaust port communicating with the valve chamber opens. Thus, an operator of the relief valve can conveniently adjust pressure to increase the actuating pressure (valve-opening pressure) for opening the valve body by a simple operation of using a finger pad to close a part of the exhaust port in the operating surface to reduce a vent area of the exhaust port.

The pressure regulating member may include, as an example, a handle protruding from the valve casing, and a thread portion that can adjust the pressing level on the biasing member according to a tightening amount. Thus, an easy operation of rotating the handle protruding from the valve casing can vary the tightening amount of the thread portion to vary the pressing level on the biasing member.

The valve casing in the present invention may be configured to have a ceiling wall that closes one end side in the cylinder axial direction and has an operating surface in which an exhaust port communicating with the valve chamber opens.

Thus, like the operating surface having the exhaust port provided in the pressure regulating member described above, pressure adjustment to increase the actuating pressure of the valve body can be performed by a simple operation of varying a vent area of the exhaust port. Also, even if a user of the relief valve grips by hand an outer peripheral surface of the cylindrical valve casing, the exhaust port in the ceiling wall is not closed, thereby ensuring safety in use.

The operating surface in the present invention may be configured to have a concave vent groove with a groove surface connected to the exhaust port.

Thus, even if a finger pad is lightly placed on an upper end opening of the vent groove opening in the operating surface, the concave groove surface that forms the vent groove communicates with the exhaust port, and thus the exhaust port is not completely blocked. Also, in various use situations, even if the entire operating surface in which the vent groove opens is, for example, brought into tight contact with a wall surface, a part of a body, clothes, a pillow, or the like and unintentionally closed, the vent groove ensures an exhaust path, and thus the exhaust gas is not completely blocked.

Also, an outer periphery of the valve casing can be gripped by hand, and the upper end opening of the vent groove opening in the operating surface can be opened/closed by a thumb or index finger pad, thereby allowing the actuating pressure of the valve body to be adjusted with high operability.

Such a relief valve can be favorably used, for example, in an artificial respirator, when air needs to be temporarily supplied with high pressure to expand a lung through which air is difficult to pass in the case of laterality in lung expansion due to narrowing of windpipe or bronchus caused by sputum or foreign matter, or lung collapse (atelectasis) caused by sputum aspiration. With the vent groove, lightly placing a finger pad on the upper end opening of the vent groove opening in the operating surface merely reduces air flowing out, and thus the exhaust air is not completely blocked. Thus, the relief value can be safely used without excessive expansion of the lung.

The valve casing in the present invention may be configured to have a taper wall having a diameter increasing from one side to the other side in the cylinder axial direction.

Accordingly, since the valve casing has the taper wall having the diameter increasing from one side to the other side in the cylinder axial direction, a valve casing can be molded without any support post even when using a 3D molding device such as an inexpensive 3D printer of a fused deposition modeling type. The taper wall may be provided over the entire length or a part of the length of the valve casing in the cylinder axial direction.

The peripheral wall portion of the valve body in the present invention may be configured to have a curve surface portion in an outer peripheral edge facing the inner peripheral surface of the valve casing.

Accordingly, even if a center of the valve body is offset or tilted in the opening/closing operation, the outer peripheral edge of the peripheral wall portion is the curved surface portion, thereby allowing proper opening/closing without the peripheral wall portion being caught on the inner peripheral surface of the valve casing.

The relief valve of the present invention may include a valve stem that is inserted through the valve body and supports the opening/closing operation of the valve body. The valve body can be displaced along the valve stem, thereby ensuring the opening/closing operation of the valve body. However, the valve stem is not essential in the relief valve of the present invention, and the valve body can be configured so that the valve chamber of the valve casing can be displaced in the axial direction. In this case, it is particularly preferable that the peripheral wall portion of the valve body has the curved surface portion. Without the valve stem, the center of the valve body tends to be offset or the valve body tends to be tilted during the opening/closing operation, and the valve body tends to be caught on the inner peripheral surface of the valve casing. However, the valve body having the curved surface portion is not caught on the inner peripheral surface and can stably operate even without the valve stem.

The relief valve of the present invention may have a vent gap between the peripheral wall portion of the valve body and the inner peripheral surface of the valve casing.

According to the present invention, the vent gap is provided between the peripheral wall portion of the valve body and the inner peripheral surface of the valve casing. Thus, when the valve body is displaced, the valve body can be smoothly opened/closed without coming into contact with the inner peripheral surface of the valve casing. Also, if the vent gap is provided uniformly over the entire peripheral wall portion, gas can be evenly released to the vent gap over the entire peripheral wall portion, thereby preventing the valve body from being out of balance due to uneven distribution of gas passages when the valve body is displaced.

The relief valve of the present invention described above can be applied to various devices as described below.

Specifically, the present invention provides an artificial respirator including the relief valve of the present invention as an artificial respiration valve.

The present invention also provides an inhalation anesthesia apparatus including the relief valve of the present invention as an artificial respiration valve.

According to the artificial respirator and the inhalation anesthesia apparatus, when air flows into lungs to increase pressure, the valve is automatically opened, and when the lungs contract to reduce the pressure, the valve can be automatically closed. Supplying a constant amount of air/oxygen from an air compressor or the like can provide a stable respiration cycle. Since a power source of the valve is air pressure and no electricity or electronic component is used, there is no risk of failure when getting wet. Also, using plastic allows mass production at low cost.

Further, the present invention provides an exercise support device including: a gas chamber member that is applied to, placed on, wrapped around a predetermined site of a human body to be expandable/contractible by gas in contact with the predetermined site of the human body; a gas supply device that supplies gas to the gas chamber member; a vent pipe that provides communication between the gas supply device and the gas chamber member, and the relief valve of the present invention connected to the vent pipe.

The gas chamber member may be a cushion, and more specifically, an airtight rubber bag. A cloth cover may be attached to the rubber bag in view of usability or the like.

According to the exercise support device, the gas chamber member may be expanded/contracted according to valve-opening pressure of the relief valve of the present invention. Such a gas chamber member may be brought into contact with the predetermined site of the human body to passively move or massage the predetermined site of the human body.

More specifically, the exercise support device of the present invention provides prevention of contracture of proximal and distal regions of upper and lower limbs, trunk, palm, neck region, or the like by expanding/contracting the gas chamber member to passively move various sites of the human body, prevention of bedsore by improved circulation, support of deep breathing (raising upper limbs by expanding/contracting the gas chamber member can expand intercostal muscle to support costal breathing. Exercise of lower limbs and trunk by expanding/contracting the gas chamber member can move abdominal organs and indirectly move diaphragm to support abdominal breathing), relaxing effects (holding the expanded/contracted gas chamber member in arms and feeling breathing rhythm can bring a relaxing state to restrain cerebral excitation). Also, the exercise support device can be used as a backup artificial respirator during emergencies and disasters.

The present invention provides a device including a pipe material having the relief valve of the present invention.

As an example of this device, the present invention provides a purification device including a blower coupled to an aeration pipe that aerates an object to be purified in a purification tank, wherein the aeration pipe includes the relief valve of the present invention.

Accordingly, opening/closing the relief valve to reduce an abnormal pressure increase due to clogging of the aeration pipe can prevent damage to the blower. Also, the abnormal pressure increase due to clogging of the aeration pipe can be detected by opening/closing sound of the relief valve, thereby facilitating inspection.

As an example of a different device, the present invention also provides a diving regulator including the relief valve of the present invention in a vent path extending from a regulator to a mouth piece.

Accordingly, when air flows into lungs to increase pressure, the relief valve can be automatically opened, and when the lungs contract to reduce the pressure, the valve can be automatically closed. This can add an automatic artificial respiration function to the diving regulator, and increase the number of lives saved in emergencies during scuba diving. Since a power source of the relief valve is air pressure and no electricity or electronic component is used, there is no risk of failure when getting wet, thereby achieving a stable operation in water. Also, using plastic allows mass production at low cost.

Advantageous Effects of Invention

According to the relief valve of the present invention and various devices including the relief valve, pressure of gas higher than set pressure can be applied to automatically smoothly open the valve body, and stably maintain the valve-opened state of the valve body to the set pressure after the valve is opened, while having a simple device structure without requiring an electric drive source for an opening/closing operation of the valve body.

BRIEF DESCRIPTION OF DRAWINGS

FIG. 5 illustrates a relief valve according to a second embodiment.

FIG. 6 illustrates a support for manufacturing a coil spring.

DESCRIPTION OF EMBODIMENTS

Now, with reference to the drawings, embodiments of the present invention will be described.

1. Embodiment of Relief Valve

First Embodiment [FIGS. 1 to 4]

[Description on Structure of Relief Valve 1]

Figure 1:
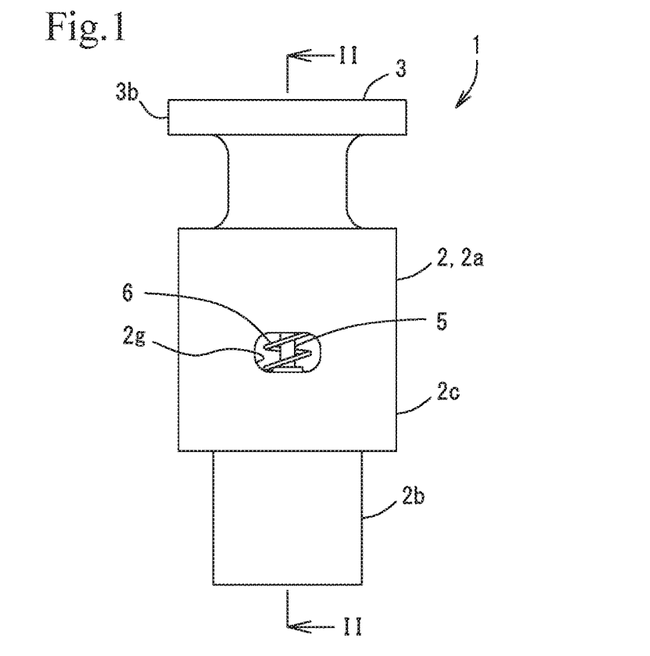
FIG. 1 is a front view of a relief valve according to a first embodiment.
Figure 2:
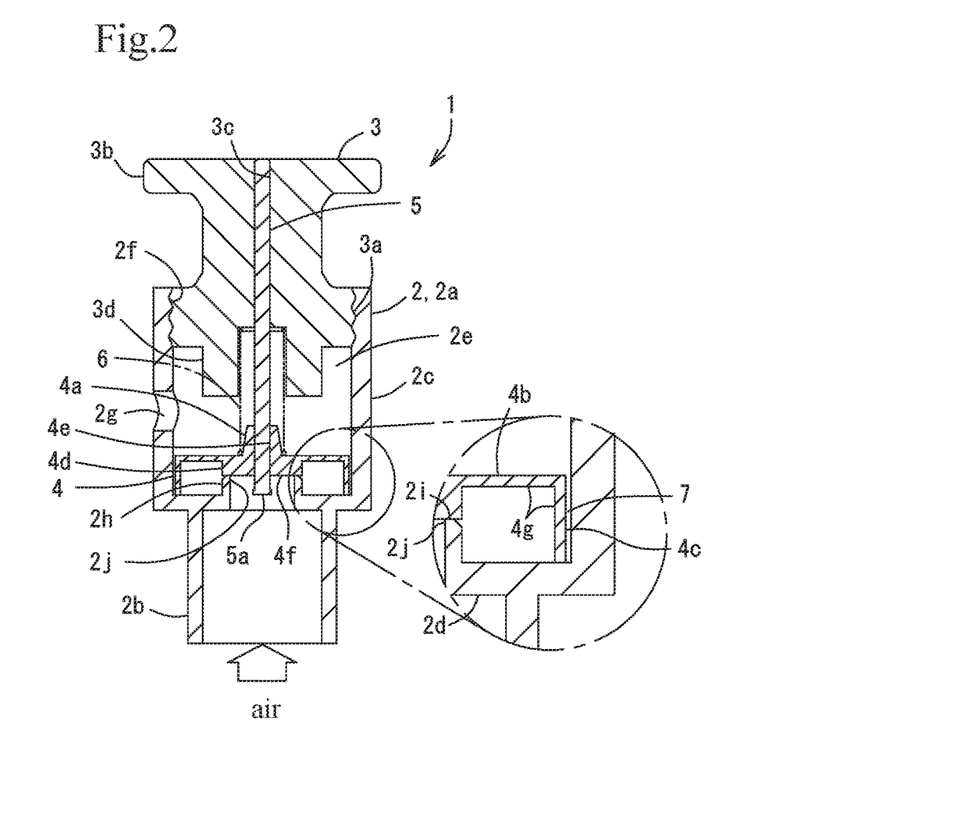
FIG. 2 is a sectional view of a valve-closed state of the relief valve taken along the line II-II in FIG. 1.

A relief valve 1 includes a valve casing 2, a handle 3 as a "pressure regulating member", a valve body 4, a valve stem 5, and a coil spring 6 as a "biasing member". In this embodiment, the valve stem 5 and the coil spring 6 are made of a metal material or resin mold, and all the other members are made of resin mold. Of course, the relief valve 1 may be completely made of a metal material. However, all the components of the relief valve 1 made of resin mold allow manufacture at low cost. Also, for example, a patient using an artificial respirator including the relief valve 1 can carry the artificial respirator when having an MRI examination, and the relief valve is not taken in an image in an X-ray examination.

The valve casing 2 is made of resin mold, and includes a closed-end cylindrical body portion 2a, and a suction port 2b protruding from a bottom wall of the body portion 2a in a concentric cylindrical shape having a smaller diameter.

The body portion 2a includes a peripheral wall 2c and a bottom wall 2d, and a valve chamber 2e is formed therein. An internal thread portion 2f is formed in an inner peripheral surface on one end side of the peripheral wall 2c. An external thread portion 3a of the handle 3 is threaded into the internal thread portion 2f. An exhaust port 2g formed of a substantially elliptical through hole is formed in an axial center of the peripheral wall 2c and communicates with the valve chamber 2e and the outside. A valve seat protrusion 2h cylindrically protruding toward the valve chamber 2e is formed on the bottom wall 2d located on the other end side of the peripheral wall 2c, and a tip of the protrusion forms a valve seat 2i on which the valve body 4 in a valve-closed state is seated. A valve hole 2j opens inside the valve seat 2i and communicates with the suction port 2b.

The handle 3 is mounted to the valve casing 2 as described above, and has an operating portion 3b protruding from the valve casing 2 and having a T-shaped section. Gripping and rotationally operating the operating portion 3b can adjust a threading level of the handle 3 in the valve casing 2. A mounting hole 3c for the valve stem 5 is axially formed through the handle 3, and the valve stem 5 inserted through the mounting hole 3c is retained therein by a set screw (not shown) or an adhesive or the like. On a side opposite to the operating portion 3b of the handle 3, a housing portion 3d of the coil spring 6 cylindrically protruding toward the valve chamber 2e is formed so as to ensure that one end side of the coil spring 6 that is elastically deformed in the valve chamber 2e can be held.

The valve body 4 includes a support protrusion 4a protruding in a truncated conical shape, a flange portion 4b laterally extending from a bottom surface of the support protrusion 4a in an annular shape, and a peripheral wall portion 4c cylindrically protruding downward from the flange portion 4b. The support protrusion 4a is inserted into the other end side of the coil spring 6, and this ensures that the other end side of the coil spring 6 that is elastically deformed can be held.

A seating portion 4d cylindrically protruding and seating on the valve seat 2i is formed on back surfaces of the support protrusion 4a and the flange portion 4b. Comparing protrusion heights of the seating portion 4d and the peripheral wall portion 4c from the flange portion 4b, the protrusion height of the peripheral wall portion 4c is larger. Thus, the back surface of the flange portion 4b and the seating portion 4d are surrounded by the peripheral wall portion 4c, and the insides thereof entirely form a large pressure receiving surface that receives pressure of gas flowing into the valve chamber 2e. An insertion hole 4e for the valve stem 5 is axially formed in the valve body 4, and the valve body 4 can be displaced to a valve-opened state and a valve-closed state along the valve stem 5 in the valve chamber 2e.

The entire back surface of the valve body 4 that is opened/closed in this manner, that is, a surface of the seating portion 4d facing the bottom wall 2d, the bottom surface of the flange portion 4b, and the inner peripheral surface of the peripheral wall portion 4c form the large pressure receiving surface that receives the pressure of the gas in the valve-opened state as described above. A surface portion of the seating portion 4d exposed to the valve hole 2j in the valve-closed state in which the seating portion 4d is seated on the valve seat 2i forms a first pressure receiving surface portion 4f that receives the pressure of the gas in the valve-closed state. In the back surface of the valve body 4, portions other than the first pressure receiving surface portion 4f form a second pressure receiving surface portion 4g that receives the pressure of the gas flowing from the valve hole 2j into the valve chamber 2e in the valve-opened state. Specifically, the surface of the seating portion 4d other than the first pressure receiving surface portion 4f, the bottom surface of the flange portion 4b, and the inner peripheral surface of the peripheral wall portion 4c form the second pressure receiving surface portion 4g.

The upper end side of the valve stem 5 that guides displacement of the valve body 4 axially opened/closed is secured to the handle 3 as described above, and the lower end is formed to have a length reaching the valve hole 2j. The valve stem 5 has such a length that even if the valve stem 5 is axially moved by rotationally operating the handle 3, the lower end thereof does not protrude from the valve hole 2j into the valve chamber 2e. This is for reliably supporting the valve body 4 irrespective of the position of the handle 3. A head 5a is formed at the lower end of the valve stem 5 so that the valve body 4 does not fall.

The coil spring 6 exerts a spring force for biasing the valve body 4 into the valve-closed state, and valve-opening pressure at which the valve body 4 is opened is adjusted by a repulsive force of the coil spring 6 pressed by the valve body 4. Specifically, the valve-opening pressure of the valve body 4 can be increased by tightening the handle 3 to compress the coil spring 6, and reduced by loosening the handle 3 to reduce preload on the coil spring 6, and an adjustment level is determined according to a device in which the relief valve 1 is used.

[Description on Operation of Relief Valve 1]

Next, the operation of the relief valve 1 will be described. When gas is supplied to the suction port 2b to increase pressure applied to the first pressure receiving surface portion 4f of the valve body 4, a force to press the valve body 4 is increased. When the force exceeds the valve-opening pressure set by the spring force of the coil spring 6, the valve body 4 is separated from the valve seat 2i at once and brought into the valve-opened state.

Figure 3:
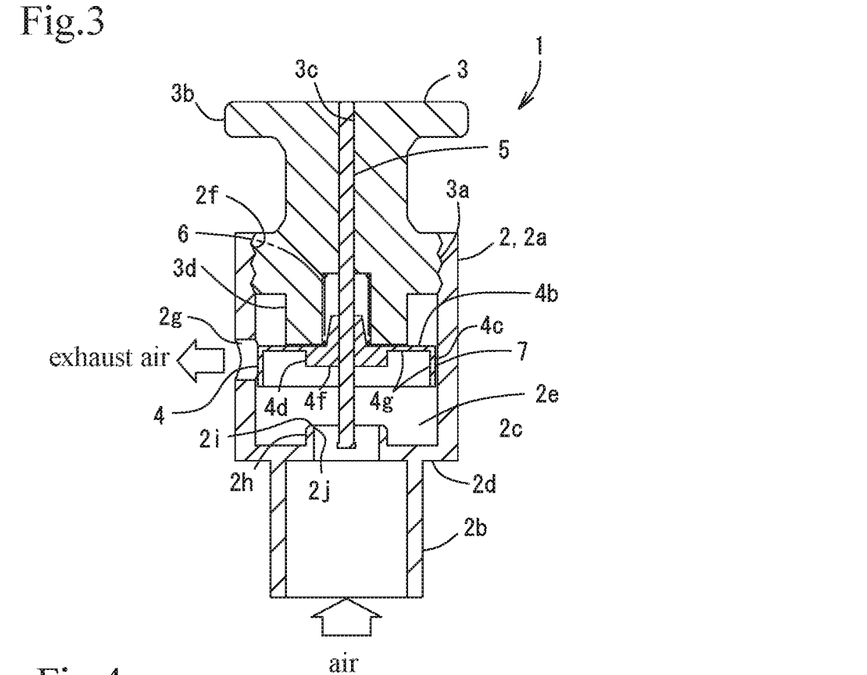
FIG. 3 is a sectional view of a valve-opened state of the relief valve taken along the line II-II in FIG. 1.

In the valve-opened state, as shown in FIG. 3, the first pressure receiving surface portion 4f and also the second pressure receiving surface portion 4g receive the pressure of the gas flowing from the valve hole 2j, and thus the valve body 4 is pushed up against the spring force of the coil spring 6 and displaced along the valve stem 5 until the flange portion 4b butts against a tip of the housing portion 3d of the handle 3. At this time, since a vent gap 7 is formed between the peripheral wall portion 4c of the valve body 4 and the inner peripheral surface of the peripheral wall 2c of the valve casing 2, the valve body 4 can be smoothly displaced without sliding on the inner peripheral surface of the peripheral wall 2c. Since the vent gap 7 in this embodiment is formed uniformly over the entire peripheral wall portion 4c, the gas can be evenly released to the vent gap 7 at regions in a circumferential direction of the peripheral wall portion 4c. This can prevent the valve body 4 from being out of balance due to uneven distribution of gas passages when the valve body 4 is displaced.

In the valve-opened state in FIG. 3, in the valve body 4, the pressure receiving area that receives the pressure of the gas flowing from the valve hole 2j is enlarged to the second pressure receiving surface portion 4g in addition to the first pressure receiving surface portion 4f. Also, the first pressure receiving surface portion 4f and the second pressure receiving surface portion 4g are surrounded by the high peripheral wall portion 4c. Thus, the entire back surface of the valve body 4 continuously receives the pressure with the pressure of the gas being reduced, thereby allowing the valve-opened state of the valve body 4 to be stably maintained. Further, the peripheral wall portion 4c of the valve body 4 is located to partially close the exhaust port 2g in the valve casing 2 so that the gas flowing from the back surface of the valve body 4 to the exhaust port 2g or the gas flowing from the upper surface of the flange portion 4b of the valve body 4 to the exhaust port 2g are difficult to be discharged out of the valve casing 2. This prevents the gas from being immediately discharged from inside the valve chamber 2e to rapidly reduce the pressure at which the valve-opened state of the valve body 4 is maintained, thereby allowing the valve-opened state of the valve body 4 described above to be more stably maintained.

Figure 4:
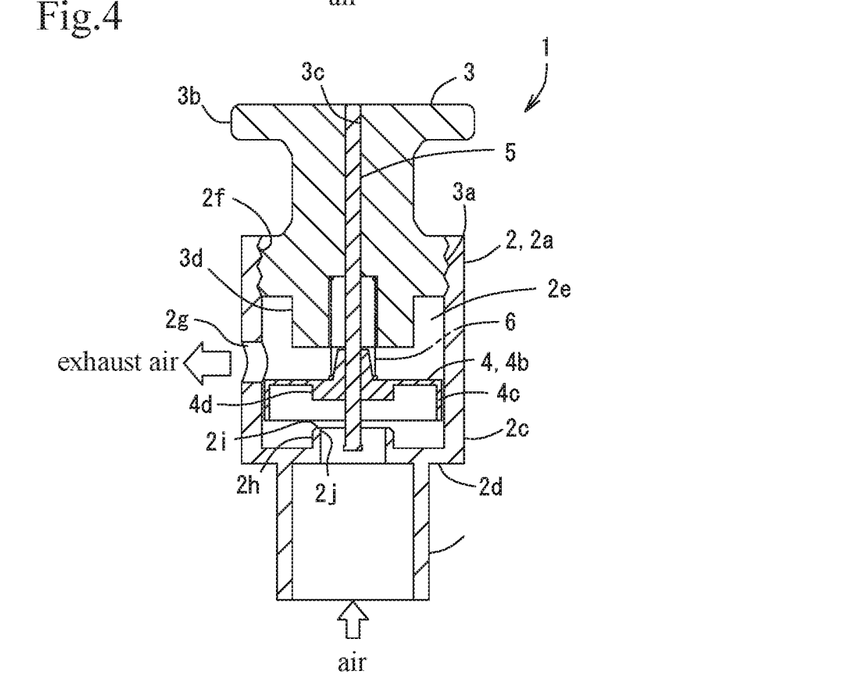
FIG. 4 is a sectional view of a closing operation of the relief valve following FIG. 3.

When the gas is gradually discharged out of the exhaust port 2g, as shown in FIG. 4, the valve body 4 is gradually pushed down toward the valve seat 2i by the coil spring 6. When the pressure becomes lower than the valve-opening pressure set by the spring force of the coil spring 6, the valve body 4 is biased by the coil spring 6 and seated on the valve seat 2i into the valve-closed state.

The opening/closing operation of the relief valve 1 has been described above. Thus, according to the relief valve 1, the pressure of the gas higher than the valve-opening pressure by the repulsive force of the coil spring 6 can be applied to automatically smoothly open the valve body 4, and stably maintain the valve-opened state of the valve body 4 to the set pressure after the valve is opened, while having a simple device structure without requiring an electric drive source for the opening/closing operation of the valve body 4.

Figure 6A:
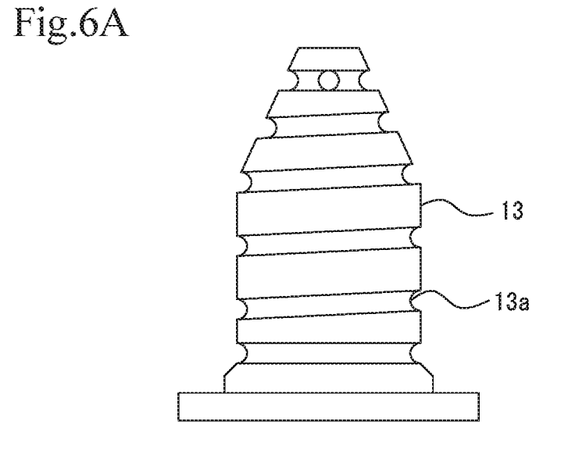
FIG. 6A is a front view.
Figure 6B:
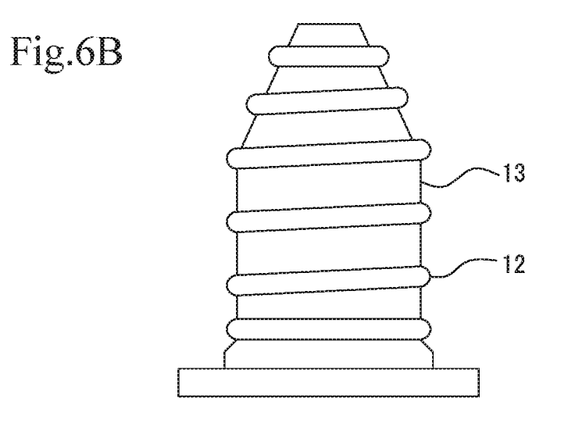
FIG. 6B is a front view of the coil spring being formed.
Figure 7:
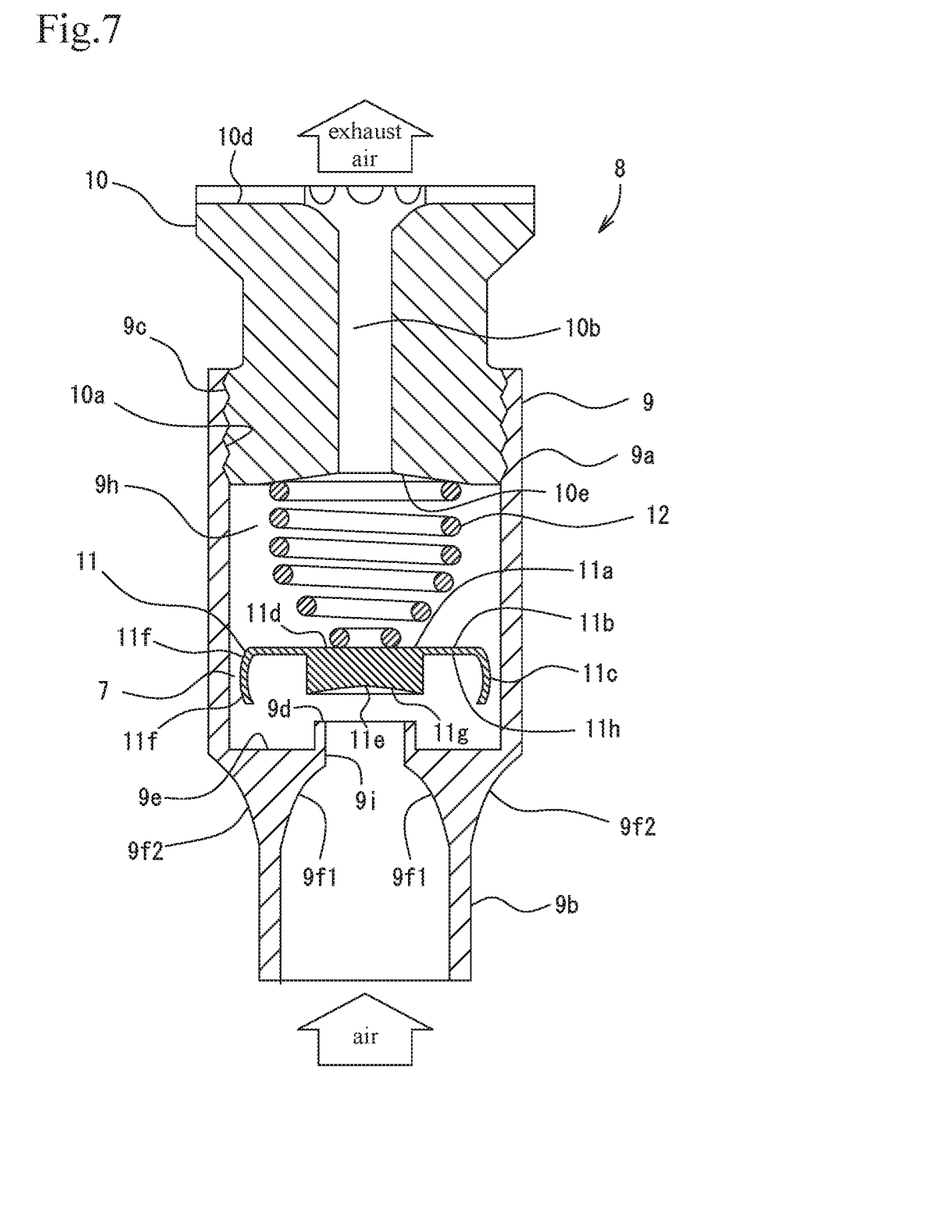
FIG. 7 illustrates an operation of the relief valve in section taken along the line VB-VB in FIG. 5.

Second Embodiment [FIGS. 5 to 7]

[Description on Structure of Relief Valve 8]

Figure 5A:
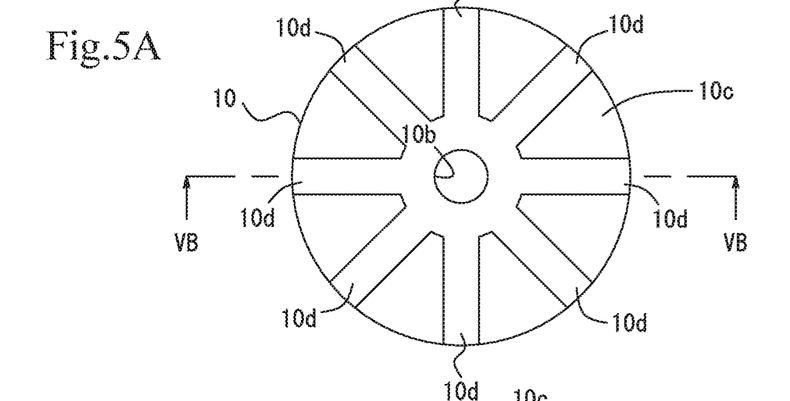
FIG. 5A is a plan view.
Figure 5B:
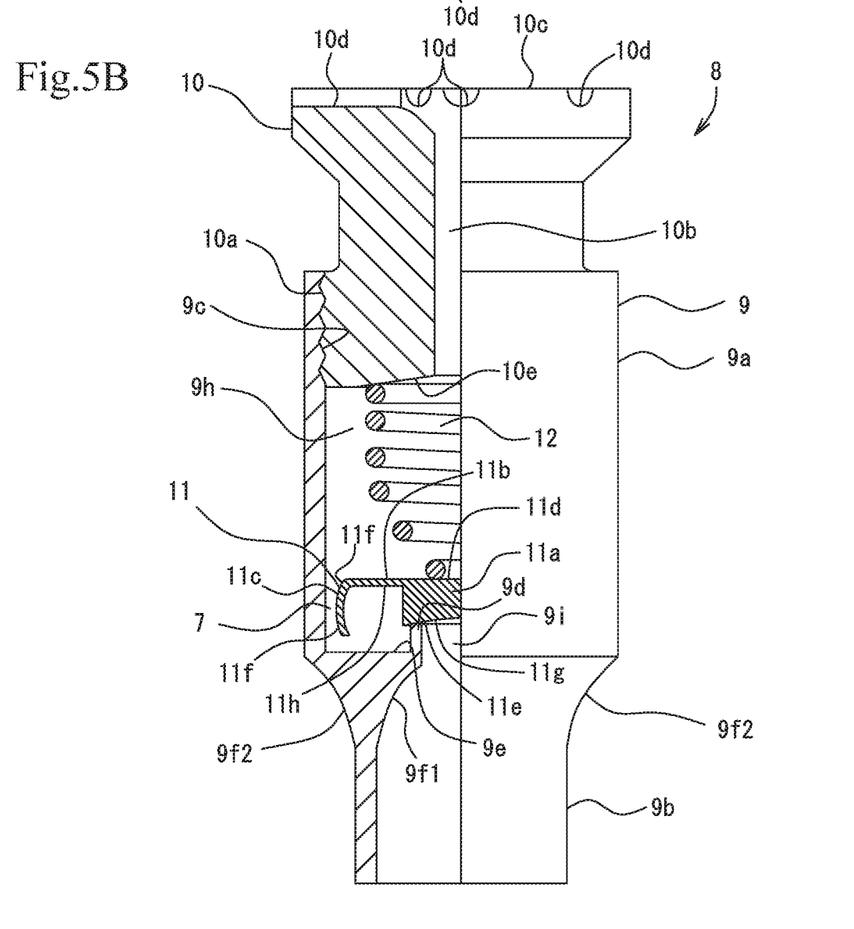
FIG. 5B is a half sectional view taken along the line VB-VB on front view.

A relief valve 8 of a second embodiment includes a valve casing 9, a handle 10 as a "pressure regulating member", a valve body 11, and a coil spring 12 as a "biasing member". In this embodiment, the valve stem 5 in the first embodiment is not provided, and the number of components is reduced. All the components of the relief valve 8 of this embodiment can be manufactured using a 3D printer. Thus, the relief valve 8 can be advantageously easily manufactured at low cost. Of course, the relief valve 8 may be made of resin mold by die molding, or a part of the components (for example, the coil spring 12) may be made of a metal material.

The valve casing 9 is formed into a cylindrical shape and includes a body portion 9a and a suction cylinder 9b. The body portion 9a is formed into a cylindrical shape having constant inner and outer diameters in a cylinder axial direction. An internal thread portion 9c is formed in an inner peripheral surface on one end side of the body portion 9a, and can be threaded on an external thread portion 10a of the handle 10 to adjust a biasing force of the coil spring 12 on the valve body 11 according to a tightening amount. A partition wall 9e having a cylindrical valve seat 9d is formed on the other end side of the body portion 9a. A taper wall 9f1 is formed on a lower surface of the partition wall 9e facing the inside of the suction cylinder 9b, in other words, on an inner peripheral surface on an upper end side of the suction cylinder 9b.

Gas flows into the suction cylinder 9b of the valve casing 9. A taper wall 9f2 is formed on an outer peripheral surface on the upper end side of the suction cylinder 9b adjacent to the body portion 9a. On the outer and inner surfaces of the valve casing 2 in the first embodiment, a step surface is formed by the bottom wall 2d radially extending between the body portion 2a and the suction port 2b, but it is difficult to form such a shape using a 3D printer. However, the valve casing 9 in this embodiment includes the taper wall 9f2 that eliminates the step surface on the outer peripheral surface of the suction cylinder 9b, and also includes the taper wall 9f1 on the partition wall 9e (the inner peripheral surface of the suction cylinder 9b), thereby allowing laminate molding using the 3D printer even without any support post. With such a shape, the valve casing 9 can be formed as a laminate printing molded article.

The handle 10 has an exhaust port 10b along a central axis. The handle 10 has the exhaust port 10b and thus the valve casing 9 has no exhaust port, which is different from the first embodiment.

An upper surface in which the exhaust port 10b of the handle 10 opens is an operating surface 10c, and concave vent grooves 10d radially extending around the exhaust port 10b are formed in the operating surface 10c. Central ends of the vent grooves 10d communicate with the exhaust port 10b, and outer peripheral ends of the vent grooves 10d open in the outer peripheral surface of the handle 10. An operator of the relief valve 8 can conveniently adjust pressure to increase actuating pressure (valve-opening pressure) for opening the valve body 11 by a simple operation of lightly placing a finger pad on the operating surface 10c to close upper end openings of the vent grooves 10d to reduce a vent area. On the other hand, even if the finger pad is lightly placed on the operating surface 10c to close the upper end openings of all the vent grooves 10d, one end side of a groove bottom of each vent groove 10d communicates with the exhaust port 10b, and the other end side opens in the outer peripheral surface of the handle 10. Thus, exhaust gas is not completely blocked, which is safe. Also, in various use situations, even if the upper end opening of the vent groove 10d is, for example, brought into tight contact with a wall surface, a part of a body, clothes, a pillow, or the like and unintentionally closed, the vent groove 10d ensures an exhaust path, and thus the exhaust gas is not completely blocked, which is safe.

A conical concave portion 10e is formed in a side opposite to the operating surface 10c of the handle 10. This is used for aligning a central axis of the coil spring 12 with a central axis of the relief valve 8.

The valve body 11 includes a circular base portion 11a against which the other end side of the coil spring 12 abuts, a flange portion 11b laterally extending from the base portion 11a in an annular shape, and a peripheral wall portion 11c cylindrically protruding downward from the flange portion 11b.

The base portion 11a has a press receiving surface 11d with which the other end side of the coil spring 12 is brought into contact and biased. An opposite surface thereof has a circular seating portion 11e that abuts against the valve seat 9d. The seating portion 11e is formed as a spherical concave. If the seating portion 11e is formed into a flat surface rather than the concave, the 3D printer molds the seating portion 11e by laminate printing with linear reciprocation in a width direction, and thus form a wavy plane with continuous minute irregularities. Then, a convex portion of the irregularities comes into contact with the valve seat 9d to cause air leakage from the concave portion, which prevents proper operation of the valve body 11. However, when forming the seating portion 11e as the spherical concave as in this embodiment, the 3D printer forms the seating portion 11e by concentric laminate printing, which does not cause the air leakage as described above. The laminate printing by the 3D printer may be performed, other than concentrically as described above, to form a hemispherical concave, a multistep annular concave, or a conical concave.

The peripheral wall portion 11c has curved surface portions 11f on a side of the flange portion 11b and a tip side. Thus, even if a center of the valve body 11 is offset or tilted in the opening/closing operation, the valve body 11 can be properly opened/closed without the outer peripheral edge of the peripheral wall portion 11c of the valve body 11 being caught on the inner peripheral surface of the valve casing 9. Also, a vent gap 7 having the same technical significance as in the first embodiment is formed between the peripheral wall portion 11c and the valve casing 9.

Comparing protrusion heights of the seating portion 11e and the peripheral wall portion 11c from the flange portion 11b, the protrusion height of the peripheral wall portion 11c is larger. Thus, a back surface of the flange portion 11b and the seating portion 11e are surrounded by the peripheral wall portion 11c, and the insides thereof entirely form a large pressure receiving surface that receives pressure of gas flowing into the valve chamber 9h. A surface portion of the seating portion 11e exposed to the valve hole 9i in the valve-closed state in which the seating portion 11e is seated on the valve seat 9d forms a first pressure receiving surface portion 11g that receives the pressure of the gas in the valve-closed state. In the back surface of the valve body 11, portions other than the first pressure receiving surface portion 11g form a second pressure receiving surface portion 11h that receives the pressure of the gas flowing from the valve hole 9i into the valve chamber 9h in the valve-opened state. Specifically, the surface of the seating portion 11e other than the first pressure receiving surface portion 11g, the bottom surface of the flange portion 11b, and the inner peripheral surface of the peripheral wall portion 11c form the second pressure receiving surface portion 11h.

The coil spring 12 has a larger diameter on the side of the handle 10 and a smaller diameter on the side of the valve body 11. Specifically, the coil spring 12 is formed as a conical spring. The coil spring 12 has the smaller diameter on the side of the valve body 11 in order to press the central side of the press receiving surface 11d of the valve body 11. The central side of the valve body 11 can be pressed to reliably press the seating portion 11e of the valve body 11 against the valve seat 9d. Thus, the outer diameter on the side of the valve body 11 of the coil spring 12 is smaller than the diameter of the seating portion 11e of the valve body 11.

Although 3D molding of the coil spring 12 using the 3D printer is very difficult, the coil spring 12 in this embodiment can be manufactured using the 3D printer as described below. Specifically, a support 13 shown in FIG. 6A is 3D-molded by the 3D printer. A spiral groove 13a in the form of the coil spring 12 is formed in an outer peripheral surface of the support 13, and a resin filament as a material for the coil spring 12 is wound around the spiral groove 13a. A slit for holding the filament is formed at a lower end of the spiral groove 13a so as to prevent the wound filament from being loosened. The filament for the 3D printer is wound around the spiral groove 13a and secured, and heated for a predetermined time suitable for the material. Thus, the coil spring 12 is formed along the spiral groove 13a of the support 13 as shown in FIG. 6B. The filament used here is preferably made of ABS resin. This is because the ABS resin changes little in spring elastic force when heated by human expired air. After the coil spring 12 is formed, an excess of the filament extending from the slit may be cut off. As such, the coil spring 12 can be also manufactured by an easy manufacturing method using the 3D printer.

[Description on Operation of Relief Valve 8]

When gas is supplied to the suction cylinder 9b of the relief valve 8 and pressure applied to the first pressure receiving surface portion 11g of the valve body 11 exceeds the valve-opening pressure of the coil spring 12, the valve body 11 is raised from the valve seat 9d into the valve-opened state (FIG. 7).

In the valve-opened state, the first pressure receiving surface portion 11g and also the second pressure receiving surface portion 11h receive the pressure of the gas, and the valve body 11 is displaced to be further raised. At this time, a vent gap 7 is formed between the peripheral wall portion 11c of the valve body 11 and the inner peripheral surface of the body portion 9a of the valve casing 9. This allows smooth displacement of the valve body 11. Since the vent gap 7 is formed uniformly over the entire peripheral wall portion 11c, the gas can be evenly released to the vent gap 7 at regions in a circumferential direction of the peripheral wall portion 11c. This can prevent the valve body 11 from being out of balance due to uneven distribution of gas passages when the valve body 11 is displaced.

In the valve-opened state in FIG. 7, in the valve body 11, the pressure receiving area that receives the pressure of the gas flowing from the valve hole 9i is enlarged to the second pressure receiving surface portion 11h in addition to the first pressure receiving surface portion 11g. Also, the first pressure receiving surface portion 11g and the second pressure receiving surface portion 11h are surrounded by the peripheral wall portion 11c. Thus, the entire back surface of the valve body 11 continuously receives the pressure with the pressure of the gas being reduced, thereby allowing the valve-opened state of the valve body 11 to be stably maintained. Further, the coil spring 12 is displaced to be contracted to hinder a flow of the gas from the valve chamber 9h to the exhaust port 10b. This prevents a rapid reduction in pressure in the valve chamber 9h, thereby allowing the valve-opened state of the valve body 11 to be more stably maintained.

When the gas is gradually discharged out of the exhaust port 10b, the valve body 11 is gradually pushed down toward the valve seat 9d by the coil spring 12. When the pressure becomes lower than the valve-opening pressure, the valve body 11 is seated on the valve seat 9d into the valve-closed state.

According to the relief valve 8, the pressure of the gas higher than the valve-opening pressure by the repulsive force of the coil spring 12 can be applied to automatically smoothly open the valve body 11, and stably maintain the valve-opened state of the valve body 11 to the set pressure after the valve is opened, while having a simple device structure without requiring an electric drive source for the opening/closing operation of the valve body 11.

All the components, other than the coil spring 12, of the relief valve 8 of this embodiment can be manufactured as 3D printing molded articles by the 3D printer. The coil spring 12 may be also easily made of a filament as a material for the 3D printer by manufacturing the support 13 as a jig using the 3D printer. Thus, the relief valve 8 of this embodiment can be easily manufactured using the 3D printer.

Variants of Embodiment

Different variants of the relief valve 1 of the first embodiment and the relief valve 8 of the second embodiment are possible and some examples thereof will be described.

For the relief valve 1 of the first embodiment, the handle 3 may be omitted, and a ceiling wall that closes the upper end opening of the valve casing 2 may be provided. In this case, the exhaust port 2g in the outer peripheral surface of the valve casing 2 is omitted, an exhaust port extending through the ceiling wall is provided, and a vent groove having a groove bottom communicating with the exhaust port is provided in an upper surface of the ceiling wall as in the second embodiment. The upper surface of the ceiling wall forms the "operating surface" in the present invention.

The eight vent grooves 10d are provided in the handle 10 of the relief valve 8 of the second embodiment, but the number of the vent grooves 10d may be larger or smaller. The concave portion 10e in the handle 10 has a spherical surface, but may have a step. Further, a portion for positioning the end of the coil spring 12 on the side of the valve body 11, which has the same function as the concave portion 10e, may be also provided in the valve body 11.

2. Embodiments of Device Including Relief Valve [FIGS. 8 and 9]

The relief valve 1, 8 may be included in an artificial respirator. The relief valve 1, 8 may be also provided as a relief valve in an anesthetic inhalation aid device proposed by the present applicant disclosed as Patent Literature 1. By the artificial respirator and the inhalation anesthesia apparatus, when air flows into lungs to increase pressure, the relief valve 1, 8 can be automatically opened, and when the lungs contract to reduce the pressure, the relief valve 1, 8 can be automatically closed. Supplying a constant amount of air/oxygen from an air compressor or the like can provide a stable respiration cycle. Since a power source of the valve is air pressure and no electricity or electronic component is used, there is no risk of failure when getting wet. Also, using plastic allows mass production at low cost.

Figure 8:
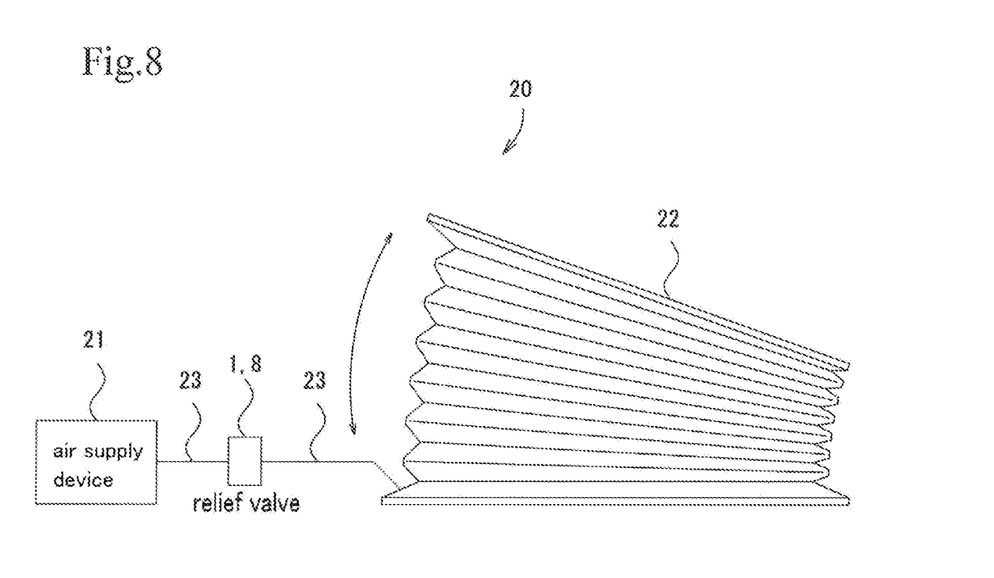
FIG. 8 illustrates an outline configuration of an exercise support device as a device including the relief valve.

Exercise Support Device [FIG. 8]

As an example of a device including the relief valve 1, 8, an exercise support device 20 will be described. As shown in FIG. 8, the exercise support device 20 includes an air supply device 21, a bellows gas chamber member 22, a vent pipe 23 connecting the air supply device 21 and the gas chamber member 22, and the relief valve 1, 8 connected to the vent pipe 23. The gas chamber member 22 may be made of an elastic material such as rubber as an example.

The relief valve 1, 8 operates as a pressure release valve, and the bellows gas chamber member 22 is expanded into a fan shape by air supplied from the air supply device 21 (the state in FIG. 8). When pressure in the gas chamber member 22 exceeds set pressure, the valve body 4, 11 is opened to discharge air in the vent pipe 23 and the gas chamber member 22 from the exhaust port 2, 10b to the outside. This contracts the gas chamber member 22. When the pressure is reduced to the set pressure, the valve body 4, 11 is closed, and air is again supplied to the gas chamber member 22 to expand the gas chamber member 22.

The gas chamber member 22 expanded/contracted in this manner can be brought into contact with a predetermined site of a human body to passively move or massage the predetermined site. More specifically, the exercise support device 20 provides prevention of contracture of proximal and distal regions of upper and lower limbs, trunk, palm, neck region, or the like by expanding/contracting the gas chamber member 22 to passively move various sites of the human body, prevention of bedsore by improved circulation, support of deep breathing (raising upper limbs by extracting/contracting the gas chamber member can expand intercostal muscle to support costal breathing. Exercise of lower limbs and trunk by expansion/contraction of the gas chamber member can move abdominal organs and indirectly move diaphragm to support abdominal breathing), relaxing effects (holding the expanded/contracted gas chamber member in arms and feeling breathing rhythm can bring a relaxing state to restrain cerebral excitation).

Figure 9:
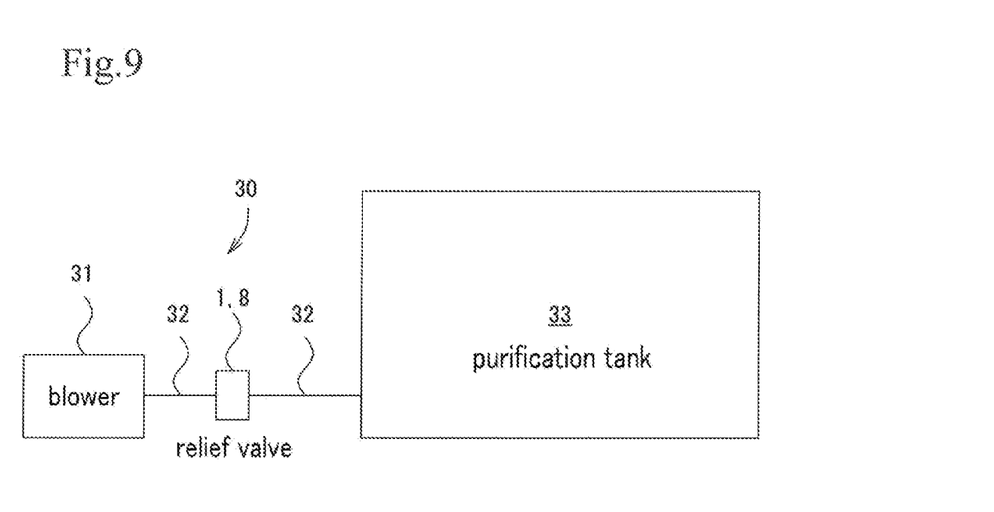
FIG. 9 illustrates an outline configuration of a purification device as a device including the relief valve.

Purification Device [FIG. 9]

As a different example of a device including the relief valve 1, 8, a purification device 30 will be described. As shown in FIG. 9, the purification device 30 includes a blower 31, an aeration pipe 32, and the relief valve 1, 8 connected to the aeration pipe 32. In this embodiment, the aeration pipe 32 communicates with an inside of a purification tank 33 that purifies an object to be purified such as dirt. In the purification device, air blown by the blower 31 is supplied by the aeration pipe 32 into the purification tank 33 to aerate the object to be purified in the purification tank 33, and thus air require for activity of aerobic microorganisms existing in the object to be purified is supplied so that the microorganisms decompose the object to be purified. The aerobic microorganisms are not essential for the purification device, but the purification device may be configured so that the blower 31 and the aeration pipe 32 are used to purify the object to be purified in the purification tank 33 by aeration.

In the purification device 30, if the aeration pipe 32 is clogged with foreign matter, the blower 31 may be damaged by an abnormal pressure increase. However, by providing the relief valve 1, 8 in the aeration pipe 32, if an abnormal pressure increase exceeding a predetermined set value occurs, the valve body 4, 11 can be opened to release and reduce pressure in the aeration pipe 32 to prevent damage to the blower 31. Also, the abnormal pressure increase due to clogging of the aeration pipe 32 can be detected by opening/closing sound of the relief valve 1, 8, thereby facilitating inspection.

Diving Regulator

A diving regulator will be described as a further example of a device including the relief valve 1, 8. Divers carry a spare regulator (octopus) in case of impaired consciousness or breathing trouble during scuba diving. However, since the octopus does not have an automatic artificial respiration function, rebreathing in water is impossible. A rescue operation cannot be performed until a diver in trouble is carried onto a boat or the ground, and thus lifesaving has been extremely difficult.

On the other hand, the diving regulator of this embodiment includes the relief valve 1, 8 in a vent path very close to a mouth piece to which air reduced in pressure by the regulator is supplied, thereby adding an automatic artificial respiration function to the diving regulator. When air flows into lungs to increase pressure, the relief valve 1, 8 can be automatically opened, and when the lungs contract to reduce the pressure, the valve can be automatically closed, thereby allowing artificial respiration even in water. Since a power source of the relief valve 1, 8 is air pressure and no electricity or electronic component is used, there is no risk of failure when getting wet, thereby achieving a stable operation in water. Also, using plastic allows mass production at low cost. The relief valve 1, 8 itself or the exhaust port provided in the relief valve 1, 8 must be mounted downward so that water stored therein is easily discharged.

REFERENCE SIGNS LIST 1 relief valve (first embodiment)
2 valve casing
2a body portion
2b suction port
2c peripheral wall
2d bottom wall
2e valve chamber
2f internal thread portion
2g exhaust port
2h valve seat protrusion
2i valve seat
2j valve hole
handle (pressure regulating member)
3a external thread portion
3b operating portion
3c mounting hole
3d housing portion
4 valve body
4a support protrusion
4b flange portion
4c peripheral wall portion
4d seating portion
4e insertion hole
4f first pressure receiving surface portion
4g second pressure receiving surface portion
5 valve stem
5a head
6 coil spring (biasing member)
7 vent gap
8 relief valve (second embodiment)
9 valve casing
9a body portion
9b suction cylinder (suction port)
9c internal thread portion
9d valve seat
9e partition wall
9f1 taper wall
9f2 taper wall
9h valve chamber
9i valve hole
10 handle (pressure regulating member)
10a external thread portion
10b exhaust port
10c operating surface
10d vent groove
10e concave portion
11 valve body
11a base portion
11b flange portion
11c peripheral wall portion
11d press receiving surface
11e seating portion
11f curved surface portion
11g first pressure receiving surface portion
11h second pressure receiving surface portion
12 coil spring (biasing member)
13 support
13a spiral groove
20 exercise support device
21 air supply device (gas supply device)
22 gas chamber member
23 vent pipe
30 purification device
31 blower
32 aeration pipe (pipe material)
33 purification tank

The invention claimed is:

1. A relief valve comprising:
a valve casing formed into a cylindrical shape and having
a suction port opening on one end side in a cylinder axial direction,
a valve hole communicating with the suction port,
a valve chamber communicating with the valve hole, and
a valve seat protruding cylindrically from a bottom surface of the valve chamber;
a valve body that closes the valve hole in a valve-closed state, and is raised in the cylinder axial direction by pressure of gas flowing from the suction port to open the valve hole; and
a biasing member that biases the valve body toward the valve hole,
wherein the valve body includes:
a seating portion where the valve seat is in contact with, and located on a back surface of the valve body;
a first pressure receiving surface portion that closes the valve hole in the valve-closed state and receives the pressure of the gas flowing from the valve hole;
a second pressure receiving surface portion that receives the pressure of the gas flowing from the valve hole into the valve chamber in a valve-opened state in which the valve body opens the valve hole; and
a peripheral wall portion that surrounds the second pressure receiving surface portion and cylindrically and downward from an outer edge of the valve body extends along an inner peripheral surface of the valve casing,
wherein the second pressure receiving surface portion is formed by at least a back surface of a flange portion extending laterally and outwardly from the seating portion in an annular shape, and an inner peripheral surface of the peripheral wall portion so as to form a large pressure receiving surface to receive the pressure of the gas in the valve-opened state.

2. The relief valve according to claim 1, further comprising a pressure regulating member that presses the biasing member that biases the valve body to provide variable actuating pressure for the valve body to open the valve hole, on the other end side of the valve casing in the cylinder axial direction,
wherein the pressure regulating member has an operating surface in which an exhaust port communicating with the valve chamber opens.

3. The relief valve according to claim 2, wherein the operating surface has a concave vent groove with a groove surface connected to the exhaust port.

4. The relief valve according to claim 1, wherein the valve casing has a ceiling wall that closes one end side in the cylinder axial direction and has an operating surface in which an exhaust port communicating with the valve chamber opens.

5. The relief valve according to claim 4, wherein the operating surface has a concave vent groove with a groove surface connected to the exhaust port.

6. The relief valve according to claim 1, wherein the valve casing has a taper wall having a diameter increasing from one side to the other side in the cylinder axial direction.

7. The relief valve according to claim 1, wherein the peripheral wall portion has a curve surface portion in an outer peripheral edge facing the inner peripheral surface of the valve casing.

8. An artificial respirator comprising the relief valve according to claim 1 as an artificial respiration valve.

9. An inhalation anesthesia apparatus comprising the relief valve according to claim 1 as an artificial respiration valve.

10. An exercise support device comprising:
- a gas chamber member that is expandable/contractible by gas and adapted to be in contact with a predetermined site of a human body;
- a gas supply device that supplies gas to the gas chamber member;
- a vent pipe that provides communication between the gas supply device and the gas chamber member, and
- the relief valve according to claim 1 connected to the vent pipe.

11. A device comprising a pipe material having the relief valve according to claim 1.

12. The relief valve according to claim 1, wherein the seating portion is cylindrically protruding on a center area of the back surface of the valve body.

13. The relief valve according to claim 1, wherein the flange portion in the valve-closed state does not contact the valve seat.

* * * * *